(12) United States Patent
Gribbon et al.

(10) Patent No.: US 6,194,001 B1
(45) Date of Patent: Feb. 27, 2001

(54) TABLET DOSAGE FORM OF CLAVULANIC ACID AND AMOXYCILLIN COMPRISING A TREHALOSE EXCIPIENT

(75) Inventors: Enda Martin Gribbon; Glen Patrick Martyn; Camilo Anthony Leo Selwyn Colaco, all of Cambridge (GB)

(73) Assignee: Quadrant Holdings Cambridge Ltd., Nottingham (GB)

( * ) Notice: Subject to any disclaimer, the term of this patent is extended or adjusted under 35 U.S.C. 154(b) by 0 days.

(21) Appl. No.: 09/230,978

(22) PCT Filed: Aug. 4, 1997

(86) PCT No.: PCT/GB97/02083

§ 371 Date: Jun. 23, 1999

§ 102(e) Date: Jun. 23, 1999

(87) PCT Pub. No.: WO98/05305

PCT Pub. Date: Feb. 12, 1998

(30) Foreign Application Priority Data

Aug. 6, 1996 (GB) .................................................. 9616536

(51) Int. Cl.[7] ..................................................... A61K 9/20
(52) U.S. Cl. ........................ 424/464; 424/465; 514/770; 514/772.3; 514/775; 514/777; 514/778; 514/779; 514/781; 514/784; 514/960; 514/970
(58) Field of Search ..................................... 424/464, 465, 424/466, 474, 480, 482; 514/970, 960

(56) References Cited

U.S. PATENT DOCUMENTS 4,678,812   7/1987   Bollin, Jr. et al. .................... 514/777

FOREIGN PATENT DOCUMENTS

| 0 415 567 | 7/1990 | (EP) . |
|---|---|---|
| 0 664 117 | 1/1995 | (EP) . |
| 0 693 558 | 1/1996 | (EP) . |
| 1 508 977 | 4/1978 | (GB) . |
| 2 005 538 | 4/1979 | (GB) . |
| 2206273 | 1/1989 | (GB) . |
| 87/00196 | 1/1987 | (WO) . |
| 92/19227 | 11/1992 | (WO) . |
| 92/22298 | 12/1992 | (WO) . |
| 95/28927 | 11/1995 | (WO) . |
| 96/22107 | 7/1996 | (WO) . |
| 97/00367 | 8/1997 | (WO) . |

*Primary Examiner*—James M. Spear
(74) *Attorney, Agent, or Firm*—Morrison & Foerster LLP

(57) ABSTRACT

Provided are tablet formulations in one embodiment comprising clavulanic acid or salt thereof, amoxycillin, and trehalose. The trehalose is, for example, amorphous anhydrous trehalose. The amorphous anhydrous trehalose is present in an amount, for example, of 5 to 50%. The formulation may further comprise, for example, desiccants, such as silica gel, or lubricants.

26 Claims, No Drawings

TABLET DOSAGE FORM OF CLAVULANIC ACID AND AMOXYCILLIN COMPRISING A TREHALOSE EXCIPIENT

This invention relates to dosage forms for pharmaceutical preparations of antibiotics, particularly but not exclusively incorporating the active ingredients potassium clavulanate and amoxycillin trihydrate. These are referred to in this specification as "co-amoxiclav" formulations. Co-amoxiclav is the British approved name or pharmacy equivalent name for formulations containing amoxycillin trihydrate and potassium clavulanate. The invention also reiazes to dosage forms of other salts or derivatives of clavulanic acid in combination with beta-lactam antibiotics.

Use of clavulanic acid in combination with beta-lactam antibiotics was disclosed in GB 1508977. WO92/19227 discloses tablet co-amoxiclav formulations comprising compacted granulates including intra-granular and extra-granular disintegrants.

GB-A-2005538 discloses co-amoxiclav formulations containing conventional excipients. U.S. Pat. No. 4,678,812 discloses replacement of mannitol with trehalose in tablets for diagnostic applications.

Potassium clavulanate is the least hygroscopic of the pharmaceutically acceptable clavulanic acid salts. Nevertheless it is extremely hygroscopic and liable to hydrolysis so that co-amoxiclav formulations are prone to degradation on storage even under low humidity conditions. The presence of water of crystallisation of amoxycillin may contribute to instability of these dosage forms, accelerating the decomposition once any degradation has commenced.

According to the present invention a tablet formulation comprises as active ingredients a combination of clavulanic acid or salt thereof and amoxycillin with excipients comprising trehalose together with further excipients including one or more binders, divalents, disintegrants and lubricants.

Trehalose ($\alpha$-D-glucopyranosyl-$\alpha$-D-glucopyranoside) is a naturally occurring, non-reducing disaccharide which was initially found to be associated with the prevention of desiccation damage in certain plants and animals which can dry out without damage and can revive when rehydrated.

Trehalose used in accordance with this invention may be provided in various physical forms. The forms of trehalose include trehalose dihydrate (TD) which is crystalline, amorphous trehalose (AT) which is a vitreous form, and the anhydrous forms of trehalose, anhydrous amorphous trehalose (AAT) and anhydrous crystalline trehalose (ACT). Powdered anhydrous trehalose may contain AAT and/or ACT. The term "trehalose" used in this specification refers to any physical form of trehalose including anhydrous, partially hydrated, fully hydrated and mixtures and solutions thereof. The term "anhydrous trehalose" refers to any physical form of trehalose containing less than 2% water. The anhydrous forms of trehalose may contain from 0 to 2% water and still retain superior properties in tabletLing. Amorphous trehalose (AT) contains about 2 to 9% water and trehalose dihydrate (TD) contains about 9 to 10% water. The manufacture and use of anhydrous trehalose from TD is disclosed in our copending application PCT/GB97/00367, the disclosure of which is incorporated into this specification by reference.

The use of trehalose, particularly amorphous anhydrous trehalose in co-amoxiclav solid dosage forms confers several advantages. Increased stability of the active ingredients, particularly potassium clavulanate is obtained. Furthermore the anhydrous trehalose protects the active ingredients from ambient humidity and any residual humidity in the formulation after manufacture. The protection from humidity offered by anhydrous trehalose (AAT or ACT) may be due to absorption of water to produce TD. This sequestration of water molecules from the active ingredients may decrease the exposure of the latter to moisture resulting in prolonged shelf life, particularly when a container is opened periodically for dispensing of some of the contents. AAT and ACT have the particular advantage that moisture is absorbed even at low relative humidities Preferably the clavulanic acid salt is potassium clavulanate.

Particularly the amoxycillin is present as amoxycillin trihydrate.

Tablets of this invention may contain the active ingredients in any convenient amounts and weight ratios. For example the weight ratio may be equivalent to amoxycillin/clavulanic acid in the range 12:1 to 1:1, preferably around 4:1 to 2:1, The proportion of active ingredients in the tablets may be between the broad range of 20 to 90 preferably about 30%. The total amount of the active ingredients may be selected to give conventional dosages including higher amounts for twice daily administration as disclosed in WO95/28927. Proportions and amounts used in this specification are by weight unless indicated otherwise.

The amount of anhydrous trehalose (AAT or ACT) may be 5 to 50%, preferably 7 to 15% more preferably about 10%.

In preferred embodiments of the invention the active ingredients, especially antibiotics, preferably clavulanate, are combined with the trehalose as a preliminary step before blending with the other components for tabletting. Dry compaction by slugging with anhydrous trehalose (AAT or ACT) may be employed, (preferably in 5 to 20% of a silica binder, conveniently Gasil 200 DF from Crosfield Ltd) using 50 to 500 $\mu$m, preferably 50 to 150 $\mu$m sieved fractions.

The flow of the blend for direct compression can be improved by selection of particle size of anhydrous trehalose (AAT or ACT) from the 125 to 500 $\mu$m, preferably 125 to 250 $\mu$m sieved fractions.

In preferred embodiments of the invention an additional excipient may be employed as a desiccant to enhance the protection for the active ingredients at higher relative humidities. A preferred additional excipient is silica gel. A low percentage may be employed, for example up to 4%, preferably below 2.5% more preferably 2.4%.

Preferred formulations incorporate one or more disintegrants. Intra-granular or extra-granular disintegrants may be employed. Suitable disintegrants include starches such as maize starch and rice starch, cross-linked N-vinyl-2-pyrrolidone (CLPVP), sodium starch glycolate, croscarmellose sodium, microcrystalline or microfine cellulose, low-substituted hydroxypropyl cellulose (ie cellulose partially substituted with 2-hydroxypropyl groups, eg less than 25% substituted, preferably 7 to 16% substituted), cross-linked sodium carboxymethyl cellulose, swellable ion exchange resins, alginates, formaldehyde-casein and combinations thereof. A preferred disintegrant is CLPVP for example as marketed under the trade names POLYPLASDONE XL and POLYPLASDONE XL-10. A preferred croscarmellose sodium is marketed under the trade name Ac-Di-Sol. A preferred sodium starch glycolate is marketed under the trade names EXPLOTAB and EXPLOTAB CLV.

The proportion of disintegrant in a tablet may be 0.1% to 30%, preferably 5 to 10%. A mixture of disintegrants may be employed. An example of a suitable disintegrant combination is a combination of micro-crystalline cellulose with sodium starch glycolate, croscarmellose sodium or CLPVP.

A lubricant may be employed. Any convenient lubricant may be used for example selected from talc, calcium stearate, stearic acid, hydrogenated vegetable oil, Lutrol and polyethylene glycol. However use of magnesium stearate is preferred. Alternatively a water soluble lubricant such as sodium stearyl fumarate (eg as sold under the trade name Pruv) may be preferred. The amount of lubricant may be optional but an amount of 0.1 to 2%, preferably 0.5% of magnesium stearate or 0.2% preferably 0.1 to 1% or 0.8% sodium stearyl fumarate may be employed.

Any of the commonly used direct compression binders may be employed including starch, cellulose derivatives (eg microcrystalline cellulose) dicalcium phosphate, calcium carbonate, magnesium carbonate and sugars such as sucrose, glucose, dextrose and lactose. Other suitable binders which may be used include Ludipress (a commercial tabletting mixture of lactose and PVP), Kollidon (polyvinyl pyrrolidone (PVP)) and hydroxyethyl starch.

Any suitable filler with a low moisture content may be employed. Use of a low moisture grade of microcrystalline cellulose, for example as sold under the trade name Avicel is preferred. This may also serve as a wicking agent. The amount of filler may be between broad limits of 10 to 90%, more preferably 20 to 50% for example 48%. Additionally and preferably a diluent such as silicon dioxide may be used. Use of the silicon dioxide sold under the trade name Gasil is advantageous. An amount of 2.5 to 30%, preferably 5 to 25% may be used.

The tablet formulations may also include other conventional excipients such as flavouring agents, sweeteners, colouring agents, preservatives and suspending aids.

Tablet formulations in accordance with this invention may comply with both BP and USP specifications and specifically to the BP specification for co-amoxiclav regular tablets.

Tablets in accordance with this invention may have a disintegration time of 60 seconds. Tablet formulations in accordance with this invention may comprise compacted granulates of a mixture of either active ingredients or a combination of both active ingredients and an intragranular disintegrant. The compacted granulates may also include single or multiple forms of trehalose. In addition the complete formulation may be granulated. The granulates formed in all cases may be subsequently compacted together into tablets with an extra-granular disintegrant. Granulates may also be used for tabletting. Preferably the clavulanate and/or amoxycillin is granulated with anhydrous trehalose and silicon dioxide. All materials can be dry blended for direct compression.

Tablets in accordance with this invention may contain an effervescent couple of a conventional type, for example a solid acid and alkaline metal carbonate or bicarbonate.

Film coated tablets may be provided. Suitable coatings include hydroxypropyl cellulose, acrylate and/or methacrylate copolymers, resins and the like. Alternatively the coating may be an enteric coating which is insoluble in acidic gastric juice but soluble in alkaline digestive juice. Such a coating may enable the antibiotic to pass through the stomach into the duodenum prior to absorption. Suitable enteric coatings include cellulose acetate phthalate.

Double-layered and press-coated tablets may also be provided. In the case of double-layered tablets the clavulanate and amoxycillin are preferably in separate layers and the clavulanate layer may contain both anhydrous trehalose and silicon dioxide. In press-coated tablets the core may contain the actives, anhydrous trehalose and silicon dioxide, and the coating may contain AT and/or TD.

Granulates of formulations in accordance with this invention may be used as free flowing granulated formulations provided in sachets or other packages. Such granulates may for example be dissolved in water with excipients, for example sweeteners, thickeners, preservatives and buffers to form syrup formulations, for example for administration to small children. The granulates may also be used in encapsulated formulations. The capsule may be an entirely conventional capsule, capable of dissolving in the stomach to release its contents, for example a soft or hard gelatin capsule.

The invention is further described by means of example but not in any limitative sense.

EXAMPLE 1

Stability of Potassium Clavulanate Blended With Different Forms of Trehalose

Potassium clavulanate (PC) was blended with either anhydrous amorphous trehalose or crystalline trehalose dihydrate. The weight ratio of trehalose to PC was 11.8:1 in both cases. Aliquots of the blended powders were stored in vacuum-sealed vials at 40° C. for a maximum period of 4 weeks. The results illustrated in FIG. 1 show that there was no significant loss in PC activity when stored under these conditions in the presence of different forms of trehalose. Sieved fractions of 50 to 500 $\mu$m, particularly 100 to 250 $\mu$m trehalose powder give advantageous flow and compatibility properties to the tabletting blend.

PC was assayed according to the USP 23 HPLC method:

Column: Hypersil ODS 5$\mu$300×4.6 mm

Detection: 220 nm

Flow Rate: 2 ml min$^{-1}$

Mobile Phase: 50 mm Phosphate Buffer (pH 4.4)/methanol:95/5(v/v)

Injection Volume: 20 $\mu$l.

All samples assayed in triplicate.

EXAMPLE 2

Protection of PC From Water Vapour by Amorphous Anhydrous Trehalose 4 g each of PC and amorphous anhydrous trehalose were weighed out into open 60 mm diameter petri dishes. A volume of water (0.4 ml) was dispensed into a third open petri dish. All 3 petri dishes were placed in a sealed container which was incubated at 25° C. After a period of 24 hours all of the water had evaporated within the sealed container. Although the amorphous anhydrous trehalose had significantly increased in weight by 40% at this time point, there was no increase in weight nor any difference in appearance in PC. These results illustrate that the evaporated water molecules were sequestered by the amorphous anhydrous trehalose. This protected the PC from detrimental interactions with water. ACT was found to take up less water than AAT at lower humidities. Blends of AAT and ACT may be used to optimise these beneficial properties.

EXAMPLE 3

Disperseble Tablet Formulation

The Following components (except for magnesium stearate) were mixed together in a planetary mixer for 10 minutes. The amorphous anhydrous trehalose was passed through a sieve with a nominal aperture size of 500 μm prior to addition to the formulation.

| COMPONENT | % W/W IN FORMULATION | WEIGHT PER TABLET (mg) |
|---|---|---|
| Amoxycillin $3H_2O$ | 17.94 | 287 |
| Potassium clavulanate | 9.31 | 148.9 |
| Microcrystalline cellulose (Avicel PH112) | 40.25 | 647.3 |
| Amorphous anhydrous trehalose | 20.0 | 320 |
| Sunett sweetener (Acesulfame K) | 1.0 | 16 |
| Strawberry flavour | 1.0 | 16 |
| Croscarmellose sodium (Ac-Di-Sol) | 1.0 | 16 |
| Sodium starch glycolate (Explotab CLV) | 3.0 | 48 |
| Polyplasdone XL (CLPVP) | 5.0 | 80 |
| Polyvinylpyrollidone (Kollidon 30) | 0.8 | 12.8 |
| Magnesium Stearate | 0.5 | 8 |

The formulation was passed through a sieve with a nominal aperture size of 500 μm. Magnesium stearate (after being passed through a sieve with a nominal aperture size of 250 μm) was then added and the formulation mixed by tumbling for 5 minutes. Tabletting was performed at ambient temperature and relative humidity using an F3 Manesty single stage tabletting press with a punch diameter of 20 mm and a compression setting of 34.

EXAMPLE 4

Dispersible Tablet Formulation

The following components (except for magnesium stearate) were mixed together in a planetary mixer for 10 minutes. The amorphous anhydrous trehalose was passed through a sieve with a nominal aperture rise of 500 μm prier to addition to the formulation.

| COMPONENT | % W/W IN FORMULATION | WEIGHT PER TABLET (mg) |
|---|---|---|
| Amoxycillin $3H_2O$ | 22.81 | 342.11 |
| Potassium clavulanate | 10.59 | 158.82 |
| Silicon dioxide (Aerosil 200) | 0.03 | 0.45 |
| Microcrystalline cellulose (Avicel PH112) | 44.27 | 664.12 |
| Amorphous anhydrous trehalose | 10.00 | 150 |
| Sunett sweetener (Acesulfame K) | 1.0 | 15 |
| Strawberry flavour | 1.0 | 15 |
| Croscarmellose sodium (Ac-Di-Sol) | 1.0 | 15 |
| Sodium starch glycolate (Explotab CLV) | 3.0 | 45 |
| Polyplasdone XL (CLPVP) | 5.0 | 75 |
| Polyvinylpyrollidone (Kollidon 30) | 0.8 | 12 |
| Magnesium Stearate | 0.5 | 7.5 |

The formulation was passed through a sieve with a nominal aperture size of 500 μm. Magnesium stearate (after being passed through a sieve with a nominal aperture size of 250 μm) was then added and the formulation mixed by tumbling for 5 minutes. Tabletting was performed at ambient temperature and relative humidity using an F3 Manesty single stage table,ting press with a punch diameter of 20 mm and a compression setting of 44. The resulting tablets had the following characteristics:

| TABLET CHARACTERISTIC | VALUE |
|---|---|
| Weight | 1.52 g |
| Thickness | 5 mm |
| Hardness | 8.6 kp |
| Dissolution test* | passes |
| Disintegration time | 1.5 min |
| Content uniformity* | passes |
| Dispersion test* | passes |

*Assays performed according to BP specification for co-amoxiclav regular tablets.

EXAMPLE 5a

Dispersible Tablet Formulation

The following components (except for magnesium stearate) were mixed together in a planetary mixer for 10 minutes. The amorphous anhydrous trehalose was passed through a sieve with a nominal aperture size of 500 μm prior to addition to the formulation.

| COMPONENT | % W/W IN FORMULATION | WEIGHT PER TABLET (mg) |
|---|---|---|
| Amoxycillin $3H_2O$ | 19.87 | 298.06 |
| Potassium clavulanate | 10.59 | 158.82 |
| Silicon dioxide (Aerosil 200) | 0.05 | 0.75 |
| Microcrystalline cellulose (Avicel PH112) | 47.99 | 719.87 |
| Amorphous anhydrous trehalose | 10.00 | 150 |
| Sunett sweetener (Acesulfame K) | 1.0 | 15 |
| Strawberry flavour | 1.0 | 15 |
| Croscarmellose sodium (Ac-Di-Sol) | 1.0 | 15 |
| Sodium starch glycolate (Explotab CLV) | 3.0 | 45 |
| Polyplasdone XL (CLPVP) | 5.0 | 75 |
| Magnesium Stearate | 0.5 | 7.5 |

The formulation was passed through a sieve with a nominal aperture size of 500 μm. Magnesium stearate (after being passed through a sieve with a nominal aperture size of 250 μm) was then added and the formulation mixed by tumbling for 5 minutes. Tabletting was performed a; ambient temperature and relative humidity using an F3 Manesty single stage tabletting press with a punch diameter of 20 mm and a compression settling of 46. The resulting tablets had the following characteristics:

| TABLET CHARACTERISTICS | VALUE |
|---|---|
| Weight | 1.5 g |
| Thickness | 5 mm |
| Hardness | 11.6 kp |
| Dissolution test* | passes |
| Disintegration time | 1.5 min |

-continued

| TABLET CHARACTERISTICS | VALUE |
|---|---|
| Content uniformity* | passes |
| Dispersion test* | passes |

*Assays performed according to BP specification for co-amoxiclav regular tablets.

EXAMPLE 5b

Dispersible Tablet Formulator

The following components selected to give a tablet of 100% were mixed together (except for Pruv) in a planetary mixer for 10 minutes. The amorphous anhydrous trehalose was passed through a sieve with a nominal aperture size of 500 μm prior to addition to the formulation.

| COMPONENT | % W/W IN FORMULATION |
|---|---|
| Amoxycillin 3H$_2$O | 19.87 |
| Potassium clavulanate | 10.59 |
| Silicon dioxide (Aerosil 200) | 0.3 |
| Microcrystalline cellulose (Avicel PH112) | 27–47.99 |
| Anhydrous trehalose | 10–20 |
| Sunett sweetener (Acesulfame K) | 1.0 |
| Strawberry flavour | 1.0 |
| Croscarmellose sodium (Ac-Di-Sol) | 5 |
| Polyplasdone XL (CLPVP) | 4 |
| Sodium stearyl fumarate (Pruv) | 0.5–1 |
| Silicon dioxide diluent (Gasil 200 DF) | 5–30 |

The formulation was passed through a sieve with a nominal aperture size of 50 μm to remove fines. Pruv (after being passed through a sieve with a nominal aperture size of 250 μm) was then added and the formulation mixed by tumbling for 5 minutes. Tabletting was performed at ambient temperature and relative humidity using an F3 Manesty single stage tabletting press with a punch diameter of 20 mm and a compression setting of 46. The resulting tablets showed good dissolution, dispersion and storage stability.

| TABLET CHARACTERISTIC | VALUE |
|---|---|
| Weight | 1.55 g |
| Thickness | 5 mm |
| Hardness | 8.2 kp |
| Dissolution test* | passes |
| Disintegration time | 1 min |
| Content uniformity* | passes |
| Dispersion test* | passes |

*Assays performed according to BP specification for co-amoxiclav regular tablets.

EXAMPLE 6

Dispersible Tablet Storage Stability

Batches of tablets made in accordance with Example 5 were stored in sealed containers, together with commercially available tablets with similar levels of actives. Storage was at 40° C. and 75% relative humidity. After 2 weeks storage, 2 liter stock solutions were prepared using 10 of each batch of tablets (refer to FIG. 2). It was evident that there was marked discolouration in the reference tablet solution whereas that of the invention tablet remains white. The brown discoloration was due to potassium clavulanate inactivation. This indicated that the stability of potassium clavulanate in the invention tablet had been markedly enhanced.

EXAMPLE 7

Dispersable Tablet With Additional Desiccant

Two batchtes with varying amounts of AAT blended with pre-dried excipients were prepared designated Example 7a and 7b.

One batch included silica gel at 2.4% w/w. This was designated Example 7c.

The batches for Examples 7a–c were redried in a Precision Scientific oven at 60° C. for 1 week. Ten tablets of each batch were placed in a minimal head-space glass jar and sealed with Nescoflim prior to testing. Ten tablets were treated identically and placed at 4° C. to act as controls. Five tablets were removed from each of the jars and assayed by HPLC for amoxycillin and potassium clavulanate content.

The blend was then tabletted using the Manesty F3 operated manually:

Compression:48.5 fill wt: 1.50–1.51 g punches 20mm bevel edged

Testing of tablets:

The following specification was applied:

disintegration time: less than one minute.

dispersion test: pass through 710 micron sieve.

hardness: 5–7 kP residual moisture content (rmc) was determined

The tablets were formulated according to the following method.

A) Pass the 30# AAT and amoxycillin trihydrate through a 30# sieve and mix for 5 mins by hand. Then re-sieve and mix for a further 2 min and set aside.

B) Sieve the Aerosil 200 and potassium clavulanate through a 30# sieve and mix for 5 min. Then re-sieve and mix for a further 5 min.

C) Combine (A) with approximately 75% of the Avicel PH-112 and mix for 5 min.

D) Mix in a weigh-boat with a spatula the Sunnett, strawberry hexaflavour, Ac-Di-Sol, Explotab and CL-PVP with the remaining 25% of the Avicel.

E) Combine (C) and (D) and mix for 5 min.

F) Combine (E) and (B) and mix for 5 min. Sieve through a 30# sieve and re-mix for a further 5 min.

G) Sieve the magnesium stearate through a 250 micron sieve and mix into (F) with minimal blending for 1 min.

EXAMPLE 7a

| Ingredient | % w/w | mg/tablet | weight (g) |
|---|---|---|---|
| Amoxycillin. 3H$_2$O | 19.87 | 298.06 | 19.87 |
| Potassium Clavulanate | 10.59 | 158.82 | 10.59 |
| Aerosil 200 | 0.05 | 0.75 | 0.05 |

-continued

| Ingredient | % w/w | mg/tablet | weight (g) |
|---|---|---|---|
| Avicel-PH112 | 47.99 | 719.87 | 47.99 |
| AAT (30# sieved) | 10.00 | 150 | 10.00 |
| Sunnett Acesulfame K | 1.00 | 15 | 1.00 |
| Strawberry hexaflavour | 1.00 | 15 | 1.00 |
| Ac-Di-Sol | 1.00 | 15 | 1.00 |
| Explotab | 3.00 | 45 | 3.00 |
| CL-PVP | 5.00 | 75 | 5.00 |
| Magnesium Stearate | 0.50 | 7.5 | 0.50 |

EXAMPLE 7b

| Ingredient | % w/w | mg/tablet | weight (g) |
|---|---|---|---|
| Amoxycillin.$3H_2O$ | 19.87 | 298.06 | 9.94 |
| Potassium Clavulanate | 10.59 | 158.82 | 5.30 |
| Aerosil 200 | 0.05 | 0.75 | 0.025 |
| Avicel-PH112 | 42.99 | 322.5 | 21.50 |
| AAT (30# sieved) | 15.00 | 112.5 | 7.50 |
| Sunnett Acesulfame K | 1.00 | 15 | 0.50 |
| Strawberry Hexaflavour | 1.00 | 15 | 0.50 |
| Ac-Di-Sol | 1.00 | 15 | 0.50 |
| Explotab | 3.00 | 45 | 1.50 |
| CL-PVP | 5.00 | 75 | 2.5 |
| Magnesium Stearate | 0.50 | 7.5 | 0.25 |

Example 7b passed all the tests. The rmc was 4.6% w/w.

EXAMPLE 7c

| Ingredient | % w/w | mg/tablet | weight (g) |
|---|---|---|---|
| Amoxycillin.$3H_2O$ | 19.87 | 298.06 | 9.94 |
| Potassium Clavulanate | 10.59 | 158.82 | 5.30 |
| Aerosil 200 | 0.05 | 0.75 | 0.025 |
| Avicel-PH112 | 45.59 | 342 | 22.80 |
| AAT (30# sieved) | 10.00 | 75 | 5.00 |
| Syloid AL1-FP | 2.40 | 36 | 1.20 |
| Sunnett Acesulfame K | 1.00 | 15 | 0.05 |
| Strawberry hexaflavour | 1.00 | 15 | 0.50 |
| Ac-Di-Sol | 1.00 | 15 | 0.50 |
| Explotab | 3.00 | 45 | 1.50 |
| CL-PVP | 5.00 | 75 | 2.5 |
| Magnesium Stearate | 0.50 | 7.5 | 0.25 |

Example 7c passed the tests. The mean rmc was 5.5% w/w.

HPLC Analysis of Examples 7a–c

The results of HPLC analysis of the drug actives are shown as mean % of USP specification for both amoxycillin and potassium clavulanate.

| Mean Potassium Clavulanate content as % of USP spec | 4° C. 1 month |
|---|---|
| 9M13A | 98.59 |
| 9M16A | 97.92 |
| 9M18A | 100.54 |
| 9M19A | 98.80 |

| Mean Amoxycillin content as % of USP | 4° C. |
|---|---|

| spec | 1 month |
|---|---|
| 9M13A | 104.07 |
| 9M16A | 101.53 |
| 9M18A | 97.47 |
| 9M19A | 95.44 |

Method of granulate preparation a) active components were milled and sieved using a 1.0 or 0.7 mm aperture sieve b) mix for 15 minutes in a blender with the chosen intra-granular disintegrant (eg CLPVP)

c) the blended mixture was then consolidated using a roller compacter at a controlled pressure (eg 50 KN)

d) the compacted flakes were then granulated in a mill, or granulated through a sieve Fitted with a 1 mm mesh to obtain a suitable size fraction.

The size of the resultant granulates are preferably in the range 100 μm to 2 mm, suitably around 1 mm+/−0.25 mm. The particle size of the actives in the granulates is preferably in the range 5 μm to 500 μm, especially 5.0 μm to 200 μm.

Suitable disintegrants include those described previously or combinations thereof. The proportion of intra-granular disintegrant in the granulate may be 0.1–10 wt % of the granulate, suitably 1.0–9.0 wt %, such as 1.5–4.0 wt %. The proportion of extra-granular disintegrant to total tablet weight may vary between broad limits, for example 0.1–30 wt %.

Preferred combinations of components for the tablets of this aspect of the invention therefore comprise:

GRANULATE 1

| COMPONENT | WEIGHT % | EXAMPLE |
|---|---|---|
| Antibiotics | 70–99 | Amoxycillin trihydrate and/or Potassium clavulanate |
| Disintegrant(s) | 0.1–4 | CLPVP, microcrystalline cellulose, sodium starch glycolate, croscarmellose sodium |
| Diluent(s) | 0–30 | trehalose: AT, AAT, TD, ACT or mixtures thereof |

TABLET 1

| COMPONENT | WEIGHT % | EXAMPLE |
|---|---|---|
| Granulate | 70+ | above |
| Disintegrant(s) | 0.1–25 | CLPVP, microcrystalline cellulose, sodium starch glycolate, croscarmellose sodium |
| Lubricant | 0–0.5 | Magnesium stearate |
| Excipients | to 100 | acesulfame K, aspartame, flavourings, colour, Silicon dioxide |

GRANULATE 2

| COMPONENT | WEIGHT % | EXAMPLE |
|---|---|---|
| Antibiotics | 70–99 | Amoxycillin trihydrate and/or Potassium clavulanate |
| Diluent(s) | 2.5–30 | Silicon dioxide, Gasil 200 DF |
| Excipient(s) | 0–30 | Trehalose: AT, AAT, TD, ACT or mixtures thereof |

TABLET 2

| COMPONENT | WEIGHT % | EXAMPLE |
|---|---|---|
| Granulate | 70+ | above (1 and/or 2) |
| Disintegrant(s) | 0.1–25 | CLPVP, microcrystalline cellulose, sodium starch glycolate, croscarmelloe sodium |
| Lubricant | 0–1 | Sodium stearyl fumarate Pruv) |

Addditionally, the complete formulation as outlined above, minus the lubricant and extra-granular disintegrant(s) may be compacted.

The compaction of the mixture into granulates may be by conventional dry compaction means, eg pressing, rolling, slugging extrusion etc and a suitable pressure for the compaction process is 20–250 RN eg 30–70 KN preferably 40–50 KN. It may be necessary to mill and sieve the compacted mixture after compaction in order to achieve a suitable size fraction of the granulate as outlined above.

Compression into tablets may be carried out in a conventional manner, eg on a conventional tabletting machine. A specific granulation example is:

GRANULATE

| COMPONENT | WEIGHT % |
|---|---|
| Amoxycillin.3H$_2$O | 19.32 |
| Potassium clavulanate | 10.25 |
| Amorphous anhydrous trehalose | 10.05 |
| Microcrystalline cellulose (Avicel PH112) | 53.14 |
| Sodium starch glycolate (Explotab) | 3.29 |
| Croscarmellose sodium (Ac-Di-Sol) | 3.29 |
| Flavouring | 0.66 |

TABLET

| COMPONENT | WEIGHT % |
|---|---|
| Granulate as above | 99.48 |
| Magnesium stearate | 0.52 |

The components for granulation were blended in a planetary mixer for 10 minutes. The Formulation was then compacted by passing it through a Kilian eccentric tabletting press fitted with 20 mm diameter punches. The compacted material was subsequently passed through a sieve with a nominal mesh size of 1 mm. The resulting material was blended in a planetary mixer for 5 minutes prior to tabletting. The granulate blend had the following characteristics:

| PHYSICAL CHARACTERISTIC | VALUE |
|---|---|
| Bulk volume | 2.04 ml/g |
| Bulk density | 0.49 g/ml |
| Tapped volume | 1.52 ml/g |
| Tapped density | 0.659 g/ml |
| Flowability | 0.989 g/s |
| Angle of Repose | 41.1 |
| Compressibility | 25.53% |

Tablets of 20 mm diameter were made using the Kilian eccentric tabletting press. These had the following characteristics:

| TABLET CHARACTERISTIC | VALUE |
|---|---|
| Weight | 1.52 g |
| Thickness | 4.55 mm |
| Hardness | 9.37 kp |
| Disintegration time | 1.83 min |
| Dispersion test | passes |

EXAMPLE 8

Encapsulated Formulation

A granulate or powder blend was prepared using the above methods and made into a loose compact under gentle pressure. This is subsequently sealed into gelatin capsules.

EXAMPLE 9

Sachet and Syrup Formulations

A granulate prepared using the above methods was combined with extra-granulate excipients including an extra-granular disintegrant (eg CLPVP at 0.1–5% by weight, flavourings (eg lemon, strawberry and/or peach) at 1.0–15% by weight, sweetener (eg aspartame or acesulfame K) at 0.5–2.0% by weight and optionally xanthan gum as a suspending agent at 1.0–5.0% by weight.

Additionally, these weights may be made up in a specific volume to produce a syrup with the required dose levels of antibiotics. To adjust the syrup to a suitable viscosity and pH, aerosil 200, succinic acid and/or methocel E-15 (dry) may be used.

EXAMPLE 10

Formation of of Bilayered and Press-coated Tablets

Bilayered tablets were made containing the compositions of Examples 3–5, except that magnesium stearate was replaced by sodium stearyl fumarate (Pruv) and 5–20% of the Avicel in these examples was replaced by an equivalent weight of Gasil 200 DF. The two antibiotics were contained in separate layers in the tablets. The tablets contained the clavulanate, AT (ACT or AAT), disintegrants and Gasil in one layer and the Amoxicillin, flavours, diluents and disintegrants in the other.

Press coated tablets were made according to the procedure of Remington (p1616) containing the compositions as in present Examples 3 to 5, except that magnesium stearate was replaced by Pruv and 5–20% of the Avicel in these examples was replaced by an equivalent weight of Gasil 200 DF. The cores of the press-coated tablets contained the antibiotics, flavours, disintegrants, diluent (Gasil 200) and excipients anhydrous trehalose AT (AAT or ACT) whereas the outer layer contained the anhydrous trehalose (AAT or ACT) and optionally favourings.

What is claimed is:

1. A tablet formulation comprising:

a) clavulanic acid or salt thereof;

b) amoxycillin; and c) trehalose.

2. A formulation as claimed in claim 1 wherein the trehalose is anhydrous trehalose.

3. A formulation as claimed in claim 1 wherein the trehalose is amorphous anhydrous trehalose.

4. A formulation as claimed in claim 3 wherein the amount of amorphous anhydrous trehalose is 5 to 50%.

5. A formulation as claimed in claim 4 wherein the amount of amorphous anhydrous trehalose is 7 to 15%.

6. A formulation as claimed in claim 1, further comprising a desiccant.

7. A formulation as claimed in claim 6 wherein the desiccant is silica gel.

8. A formulation as claimed in claim 6 wherein the amount of desiccant is up to 4%.

9. A formulation as claimed in claim 6 wherein the amount of desiccant is up to 2.5%.

10. A formulation as claimed in claim 1, further comprising one or more disintegrants selected from the group consisting of starches, cross-linked N-vinyl-2-pyrrollidone, sodium starch glycolate, croscarmellose sodium, microcrystalline or microfine cellulose, low substituted hydroxypropyl cellulose, crosslinked sodium carboxymethyl cellulose, swellable ion exchange resins, alginates, formaldehyde-casein and mixtures thereof.

11. A formulation as claimed in claim 10 wherein the proportion of disintegrant in the tablet is 0.1 to 30%.

12. A formulation as claimed in claim 10 wherein the proportion of disintegrants in a tablet is 5 to 10%.

13. A formulation as claimed in claim 1, further comprising a lubricant.

14. A formulation as claimed in claim 13 wherein the lubricant is magnesium stearate in a range from about 0.1% to 2%.

15. A formulation as claimed in claim 13 wherein the lubricant is water soluble sodium stearyl fumarate.

16. A formulation as claimed in claim 15 wherein the amount of sodium stearyl fumarate is 0.2%.

17. A formulation as claimed in claim 1, further comprising silicon dioxide as a diluent.

18. A formulation as claimed in claim 17 wherein the amount of silicon dioxide is 2.5 to 30%.

19. A formulation, as claimed in claim 17 wherein the amount of silicon dioxide is 5 to 25%.

20. A formulation as claimed in claim 1, wherein the ratio of clavulanic acid salt to amoxycillin is equivalent to a ratio of amoxycillin to clavulanic acid of 12:1 to 1:1.

21. A formulation as claimed in claim 1, wherein the proportion of active ingredients in the tablets is 20 to 90%.

22. A formulation as claimed in claim 4 wherein the amount of amorphous anhydrous trehalose is about 10%.

23. A formulation as claimed in claim 10 wherein the proportion of disintegrants in a tablet is about 9%.

24. A formulation as claimed in claim 15 wherein the amount of sodium stearyl fumarate is 0.1 to 1%.

25. A formulation as claimed in claim 1, wherein the ratio of clavulanic acid salt to amoxycillin is equivalent to a ratio of amoxycillin to clavulanic acid of about 4:1 to 2:1.

26. A formulation as claimed in claim 1, wherein the proportion of active ingredients in the tablets is about 30%.

* * * * *